United States Patent [19]

Cooper et al.

[11] Patent Number: 5,422,256

[45] Date of Patent: Jun. 6, 1995

[54] **PRODUCTION OF ANTHRANILIC ACID BY A STRAIN OF *BACILLUS SUBTILIS* RESISTANT TO SULFAGUANIDINE AND FLUOROTRYPTOPHAN**

[75] Inventors: Bryan Cooper, Mannheim; Joachim Meyer, Hessheim; Klaus Euler, Ludwigshafen, all of Germany

[73] Assignee: BASF Aktiengesellschaft, Ludwigshafen, Germany

[21] Appl. No.: 962,576

[22] Filed: Dec. 28, 1992

[30] Foreign Application Priority Data

Oct. 8, 1990 [DE] Germany .................. 40 31 854.0

[51] Int. Cl.⁶ .................. C12P 13/00; C12N 01/20
[52] U.S. Cl. .................. 435/128; 435/108; 435/252.5; 435/839
[58] Field of Search .................. 435/108, 128, 252.5, 435/839

[56] References Cited

U.S. PATENT DOCUMENTS 4,363,875 12/1982 Ahashiba .................. 435/108
4,618,580 10/1986 Shiio .................. 435/108

OTHER PUBLICATIONS

Bode et al., "Isolation and Characterization of Anthranilite-Excreting Mutants of Hansenula Henricii", (1980), Cell. Mol. Biol., 26, 615.
Aoki et al., "Further Characterization of Bacterial Production of Anthranilic Acid from Aniline", (1985), Agric. Biol. Chem., 49(4), 1151–1158.
Nunokawa, "Production of L-tryptophan", (1985), Chem. Abst., 103, No. 5024R.
Prasad et al., "Tryptophan catabolism during sporulation", (1970) Che. Abst.
Kumagai et al., "Manufacture of anthranilic acid with bacteria", (1990), Chem. Abst., 113, No. 57524e.
Karasawa, M. et al., "Firmentative Production of L-tryptophan", Chemical Abstracts 106: 48645y; 1986.

Primary Examiner—Marian Knode
Attorney, Agent, or Firm—Keil & Weinkauf

[57] ABSTRACT

A strain of Bacillus subtilis which is a tryptophan auxotroph, resistant to sulfaguanidine and flourotryptophan and produces anthranilic acid in a nutrient solution containing L-tryptophan, and process for the preparation of anthranilic acid by fermentation.

2 Claims, No Drawings

PRODUCTION OF ANTHRANILIC ACID BY A STRAIN OF BACILLUS SUBTILIS RESISTANT TO SULFAGUANIDINE AND FLUOROTRYPTOPHAN

The present invention relates to a mutant of *Bacillus subtilis* ATCC 6051A with the deposit number DSM 6015 at the Deutsche Sammlung von Mikroorganismen, Machescheroder Weg 1 B, D-3300 Braunschweig Germany, recognized as an international depository authority under the terms of the Budapest Treaty on the International Recognition of the Deposit of Microorganisms for the Purposes of Patent Protection and to mutants of DSM 6015 which, like DSM 6015, produce anthranilic acid in a nutrient solution containing L-tryptophan.

It is known that microorganisms can be employed for obtaining anthranilic acid (2-aminobenzoic acid) by fermentation. However, this produces either only low concentrations of anthranilic acid (JP-A 73/39692, JP-A 76/12992 and *Agric. Biol. Chem.*, 49 (1985) 1151) or in addition also by-products such as tryptophan, indoles or anthranilic acid derivatives (JP-A 73/39692 and *Cell. Mol. Biol.*, 26 (1980) 615) which impede the workup and isolation of the anthranilic acid.

The invention now has the object of providing a microorganism which produces anthranilic acid in higher concentrations and without interfering by-products.

Accordingly, the mutant DSM 6015, defined at the outset, of *Bacillus subtilis* ATCC 6051A has been found.

This mutant was deposited on Jun. 19, 1990, at the said depository.

In addition, a process for the preparation of anthranilic acid by fermentation has been found, which comprises cultivating the mutant DSM 6015 of the strain *Bacillus substilis* (sic) ATCC 6051A in the presence of L-tryptophan.

The mutant DSM 6015 can be described taxonomically as follows:
1. Appearance of the cells (liquid culture in nutrient broth at 30° C and 250 rpm observed): rods with the dimensions 0.5–0.8×1–5 μm. Irregular shapes, which can be considerably larger, occur during the course of growth.
2. Motility: non-motile.
3. Spores: observed.
4. Gram stain: positive in all phases of growth.
5. Growth on minimal medium +1.1% by weight glucose, positive in 2 to 6 days.
Composition of the minimal medium:
0.5% by weight ammonium sulfate, 0.15% by weight potassium dihydrogen phosphate, 0.36% by weight dipotassium hydrogen phosphate, 0.05% by weight magnesium sulfate 7-hydrate, 0,005% by weight manganese sulfate 1-hydrate, 0.2% by weight base element solution, 1.8% by weight agar, 0.005% by weight L-tryptophan, 0.00001% by weight biotin, 0.0001% by weight thiamine.
Composition of the trace element solution ("ES"):
200 mg/l iron(II) sulfate monohydrate, 10 mg/l zinc(II) sulfate 4-hydrate, 3 mg/l manganese(II) sulfate 1-hydrate, 30 mg/l boric acid, 20 mg/l cobalt(II) chloride 6-hydrate, 1 mg/l copper(II) chloride 2-hydrate, 2 mg/l nickel(II) chloride 6-hydrate, 3 mg/l sodium molybdate 2-hydrate, 500 mg/l EDTA in distilled water.
6. Vitamin requirement: not present.
Stimulation of growth on glucose minimal medium by addition of 0.1 mg/l biotin: very pronounced.
7. Amino-acid requirement: L-tryptophan
8. Colony morphology: flat, shiny, predominantly white-beige colonies.

Other characteristic properties correspond to those of *Bacillus subtilis* (see *Bergey's Manual of Systematic Bacteriology*, Vol. 2, 1986, page 1130).

The *Bacillus subtilis* ATCC 6051A mutant according to the invention produces, like the initial strain, as further product, which does not impede workup, acetoin (3-hydroxy-2-butanone).

The mutant DSM 6015 is obtained by several induced mutations, carried out successively, with mutagenic substances such as N-methyl-N'-nitro-N-nitrosoguanidine ("MNNG") or by UV irradiation with selections subsequent thereto in each case. This entails in a first step selection of mutants which, despite addition of 5-fluoro-DL-tryptophan which acts as antimetabolite, produce more tryptophan than they require for their own metabolism. Subsequently, in a second step these tryptophan-producing mutants are mutated further to generate resistance to sulfaguanidine which acts as antimetabolite. In a following mutation, mutants which excrete anthranilic acid in place of tryptophan and which therefore can be detected by fluorescence at 366 nm, are selected.

The process according to the invention can be carried out by usual techniques batchwise or continuously, specifically and expediently by incubation at pH 6–8, preferably at pH 6.5–7.5, and at a temperature of 25°–40° C. preferably 28°–37° C., in a liquid nutrient solution which contains L-tryptophan. Fermentation is usually carried out to accumulate the anthranilic acid to a concentration in the range from 2 to 15, preferably 3 to 10, g/l for from 36 to 72 hours.

The choice of the nutrient medium for culturing the microorganism is not critical. Besides L-tryptophan, it contains the sources of carbon and nitrogen customary for this microorganism, as well as other substances essential for growth.

Examples of sources of carbon which are used are sugars, preferably glucose, or saccharic acids such as gluconic acid. Suitable as source of nitrogen are both inorganic and organic compounds, for example ammonium salts, preferably ammonium sulfate, nitrates, corn steep liquor, yeast extract or peptones.

The nutrient medium usually also contains sulfates and/or phosphates of the elements magnesium, manganese and potassium, the trace elements iron, zinc, boron, cobalt, copper, nickel and molybdenum, which can for example be employed in the form of the abovementioned trace element solution, as well as vitamins such as biotin and/or thiamine.

L-Tryptophan is employed in the fermentation usually in the range from 5 to 500 mg/l preferably from 10 to 50 mg/l.

The ratio of the amounts of the other specified nutrients depends on the nature of the fermentation and is established in the individual case in a conventional way. For example, glucose concentrations in the range from 50 to 200 g/l are suitable for carrying out the process according to the invention, and concentrations in the range from 100 to 150 g/l are preferred. The ammonium sulfate which is preferred as source of nitrogen is employed in the range from 5 to 50 g/l, particularly from 10 to 30 g/l.

The addition of the yeast extract, which is likewise preferred as source of nitrogen, is chosen in the range from 0.5 to 5 g/l.

Magnesium sulfate heptahydrate is preferably used as source of magnesium and is generally employed in the range from 0.1 to 5 g/l, in particular from 0.5 to 2 g/l. Manganese sulfate hydrate as preferred source of manganese is used in the range from 0.01 to 1 g/l, preferably from 0.1 to 0.5 g/l. A preferred source of potassium is potassium dihydrogen phosphate which is added as component of the nutrient medium in concentrations of from 1 to 10 g/l, preferably from 2 to 5 g/l. Another is dipotassium hydrogen phosphate which is added to the nutrient medium in concentrations of from 1 to 15 g/l, particularly from 5 to 10 g/l.

The trace elements are, as a rule, used in a concentration range in each case from 0.1 to 1000 mg/l, particularly from 1 to 300 mg/l, as aqueous solution, specifically and preferably in the abovementioned composition.

It is possible to add the total amount of all the nutrients to the nutrient solution from the outset, but it is advisable to meter the nutrients in accordance with their consumption.

Anthranilic acid is usually removed from the fermentation broth by acidifying the fermentation broth with a mineral acid such as hydrochloric acid or sulfuric acid to a pH of from 1 to 3, preferably from 1.5 to 2.5, and then extracting with an organic solvent such as an ether, especially methyl tert-butyl ether, or an ester such as ethyl acetate, by known methods, for example in a countercurrent extraction system. It is subsequently advantageous first to remove the solvent by distillation. In this case, it is expedient to add a base, preferably sodium hydroxide solution, to the mixture before distillation, in order to convert the anthranilic acid into the salt form. This prevents a condensation reaction, during the distillation, of the anthranilic acid with the acetoin which is likewise produced by the microorganism. After the distillation, the anthranilic acid can be liberated again by acidification, preferably with hydrochloric acid. The anthranilic acid is then as a rule isolated by precipitation and filtration in a temperature range from 5° to 15° C. it being possible to assist the precipitation by adding solvents, such as toluene, in which the anthranilic acid is sparingly soluble or insoluble. The acetoin by-product can, as a rule, be removed from the remaining mixture by distillation.

Anthranilic acid is an intermediate with a wide variety of uses, for example in preparation of pharmaceuticals, cosmetics and a number of dyes. Acetoin is used, for example, as flavoring to improve the taste of margarine.

EXAMPLE 1

Cultivation and isolation of the mutant DSM 6015 suitable for the invention a) Mutagenesis of the initial strain 20 ml of a sterile aqueous nutrient medium (called nutrient medium I hereinafter), which had the following composition:

| Nutrient medium I: | |
| --- | --- |
| Glucose | 11 g/l |
| Ammonium sulfate | 5 g/l |
| Magnesium sulfate heptahydrate | 0.5 g/l |
| Magnesium sulfate hydrate | 0.05 g/l |

| -continued | |
| --- | --- |
| Nutrient medium I: | |
| Potassium dihydrogen phosphate | 1.5 g/l |
| Dipotassium hydrogen phosphate | 3.6 g/l |
| Trace element solution | 2 ml/l |
| Biotin | 0.1 mg/l |
| Thiamine | 1 mg/l | were inoculated, using a loop, with the strain *Bacillus subtilis* ATCC 6051A and incubated at 30° C. in a shaking apparatus at 200 rpm. Then, after 16 h, 1 ml of a 4% by weight aqueous MNNG solution was added. The culture was then shaken for a further 10 min. After this, the complete culture was centrifuged, and the supernatant was discarded. The centrifuged cells were dispersed in 20 ml of nutrient medium I which had been cooled to 4° C. and were again centrifuged. This separation process was repeated. The centrifuged cells were then taken up in 20 ml of an aqueous solution which contained 10% by weight glycerol and 5% by weight lactose. This suspension contained $10^7$ viable cells per 1 ml.

b). Selection by the antimetabolite 5-fluoro-DL-tryptophan 0.1 ml portions of the suspension obtained in a) were then distributed on 100 agar plates which contained the following medium: nutrient medium I, 18 g/l agar and 50 mg/l 5-fluoro-Dl-tryptophan. The plates prepared in this way were then incubated at 30° C. for 5 days.

c) Isolation and multiplication of the selected mutants

The 5 largest colonies in each case which also formed satellite colonies were transferred singly into 100 ml flasks which each contained 20 ml of nutrient medium II composed of nutrient medium I and, in addition, 11 g/l glucose, 5 g/l ammonium sulfate and 0.2 g/l Soytone (standardized soy peptone supplied by Difco) and shaken at 200 rpm at 30° C. for 2 days. After this time, the tryptophan concentrations in each of the flasks was determined by HPLC, and the mutant M1 which produced most L-tryptophan (0.2 g/l) under these conditions was isolated.

d) Enhancement of tryptophan production

The mutant M1 was subjected to a mutagenesis in analogy to the described process. 0.1 ml portions of this suspension obtained thereafter were then plated out on 50 plates containing nutrient medium II to which in addition 18 g/l agar and 200 mg/l sulfaguanidine were added. The plates prepared in this way were then incubated at 30° C. for 5 days. Colonies which were distinguished by resistance to sulfaguanidine were transferred singly into 100 ml flasks, each of which contained 20 ml of nutrient medium II, and were shaken at 200 rpm and 30° C. for 2 days. After this time, the tryptophan concentrations were determined as above, and the mutant M2 which produced most L-tryptophan (0.5 g/l) was isolated.

e) Mutation and selection to generate anthranilic acid-producing mutants.

The mutant M2 was likewise subjected to a mutagenesis by the process described under a). The suspension resulting from this was incubated at 30° C. for 5 days as indicated under b), with the difference that the nutrient medium contained no antimetabolites. Selection was carried out by irradiation with light of wavelength 366 nm. Those colonies which showed a blue fluorescence with this were isolated. They were transferred singly into 100 ml flasks, each of which contained 20 ml of nutrient medium II and 10 mg/l L-tryptophan, and were shaken at 200 rpm and 30° C. for two days. After this time, the anthranilic acid concentrations were determined, and the mutant M3 which produced most anthranilic acid (0.25 g/l) was isolated.

f) Enhancement of anthranilic acid production

The mutant M3 was mutated and selected in analogy to the process described under e). The colonies selected in this case were transferred singly into 100 ml flasks, each of which contained 20 ml of nutrient medium II and 500 mg/l L-tryptophan, and were shaken at 200 rpm at 30° C. for 2 days. After this, the anthranilic acid concentrations were determined, and the mutant M4 which produced most anthranilic acid (1 g/l) was isolated.

The mutant M4 was shaken in a 100 ml shaking flask containing 20 ml of nutrient medium II and 10 mg of L-tryptophan at 200 rpm and 30° C. for 2 days. Subsequently, 0.1 ml portions of the suspension obtained from this were plated out on 100 agar plates which contained nutrient medium II, 500 mg/l L-tryptophan and 18 g/l agar. The plates prepared in this way were then incubated at 30° C. for 3 days. The 200 largest colonies were each shaken in 100 ml flasks, each of which contained 20 ml of nutrient medium II and 10 mg of L-tryptophan, at 200 rpm and 30° c. for 2 days. From these was isolated the mutant M5 which produced 1.5 g/l anthranilic acid and 10 g/l acetoin, and was deposited under the name DSM 6015.

EXAMPLE 2

Preparation of anthranilic acid in a fermenter

A 14 liter fermenter was charged with 9.8 l of sterile aqueous nutrient solution which contained the following components:

| | |
|---|---|
| Glucose | 1,200 g |
| Ammonium sulfate | 200 g |
| Potassium dihydrogen phosphate | 30 g |
| Dipotassium hydrogen phosphate | 72 g |
| Yeast extract | 10 g |
| Magnesium sulfate heptahydrate | 10 g |
| Manganese sulfate hydrate | 1 g |
| Trace element solution | 40 ml |

| -continued | |
|---|---|
| L-tryptophan | 320 mg |

A preculture was prepared from 200 ml of the same nutrient solution by inoculation with the mutant DSM 6015 (compare Example 1). It was incubated at 200 rpm and 37° C. for 16 h. The 14 l fermenter was inoculated with this preculture and operated at 37° C. and 750 rpm, passing 1 part by volume of air per part by volume of reactor and per minute to the solution. During this, this pH was adjusted to pH 7 by automatic control with a 20% by weight NaOH solution.

After 60 h, the fermentation was stopped by acidification to pH 2 with sulfuric acid. The concentrations of the products which had been formed were determined by HPLC in the usual way. In this case, the concentration of anthranilic acid was 3.5 g/l, and that of acetoin was 25 g/l, in the fermentation broth.

This solution was extracted with 100 l of methyl tert-butyl ether at room temperature. The organic extract was then mixed with 3.1 l of a 1N NaOH solution and subsequently the methyl tert-butyl ether was distilled out under atmospheric pressure. 300 ml of toluene were then added to the alkaline solution. The solution was subsequently acidifed to pH 3.5 at 10° C. with 50% concentrated hydrochloric acid and stirred at this temperature for 3 hours. The precipitated anthranilic acid was filtered off, washed with 500 ml of cold toluene and freed of solvent at 60° C. under 1 mbar. The result was 29 g of anthranilic acid (characterized by $^1$H-NMR spectroscopy and HPLC) with a melting point of 133 to 135° C. (Lit.: 146.1° C., Chemikerkalender) and a purity of 94% (HPLC).

The residue was subjected to distillation, resulting in 115 g of acetoin with a purity of 90% (HPLC).

We claim:

1. A microbial process for the fermentative preparation of anthranilic acid, which comprises culturing a strain of *Bacillus subtilis* having all the identifying characteristics of *Bacillus subtilis* DSM 6015, in a nutrient medium containing L-tryptophan, until anthranilic acid is produced, and recovering said anthranilic acid.

2. A biologically pure culture of a strain of *Bacillus subtilis* having all the identifying characteristics of *Bacillus subtilis* DSM 6015 deposited at the Deutsche Sammlung yon Mikroorganismen in Braunschweig, Germany.

* * * * *

UNITED STATES PATENT AND TRADEMARK OFFICE
CERTIFICATE OF CORRECTION

PATENT NO.: 5,422,256

DATED: June 6, 1995

INVENTOR(S): COOPER et al.

It is certified that error appears in the above-identified patent and that said Letters Patent is hereby corrected as shown below:

On the cover sheet, insert the following PCT information:

[22] PCT Filed: Sep. 30, 1991

[86] PCT No.: PCT/EP91/01863
§ 371 Date: Dec. 28, 1992
§ 102(e) Date: Dec. 28, 1992

[87] PCT Pub. No.: WO 92/06207
PCT Pub. Date: Apr. 16, 1992

Column 6, claim 2, line 4, delete "yon" and substitute --von--.

Signed and Sealed this

Fifth Day of September, 1995

*Attest:*

BRUCE LEHMAN

*Attesting Officer*   *Commissioner of Patents and Trademarks*